(12) United States Patent
Hund et al.

(10) Patent No.: US 12,105,096 B2
(45) Date of Patent: Oct. 1, 2024

(54) RATIOS OF sFlt-1 TO P1GF OR ENDOGLIN TO P1GF AS BIOMARKERS FOR PREECLAMPSIA RELATED ADVERSE OUTCOMES AFTER BIRTH

(71) Applicant: Roche Diagnostics Operations, Inc., Indianapolis, IN (US)

(72) Inventors: Martin Hund, Horw (CH); Thomas Dieterle, Freiburg (DE); Olav Lapaire, Binningen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 41 days.

(21) Appl. No.: 16/998,444

(22) Filed: Aug. 20, 2020

(65) Prior Publication Data

US 2020/0378981 A1    Dec. 3, 2020

Related U.S. Application Data

(63) Continuation of application No. 15/216,980, filed on Jul. 22, 2016, now abandoned, which is a continuation of application No. PCT/EP2015/051457, filed on Jan. 26, 2015.

(30) Foreign Application Priority Data

Jan. 24, 2014   (EP) .................................... 14152447

(51) Int. Cl.
    *G01N 33/68*    (2006.01)
(52) U.S. Cl.
    CPC ....... *G01N 33/689* (2013.01); *G01N 33/6863* (2013.01); *G01N 2333/515* (2013.01); *G01N 2333/705* (2013.01); *G01N 2333/91205* (2013.01); *G01N 2800/368* (2013.01); *G01N 2800/50* (2013.01)

(58) Field of Classification Search
    None
    See application file for complete search history.

(56) References Cited

U.S. PATENT DOCUMENTS

| | | | |
|---|---|---|---|
| 4,016,043 | A | 4/1977 | Schuurs et al. |
| 4,018,653 | A | 4/1977 | Mennen |
| 4,424,279 | A | 1/1984 | Bohn et al. |
| 5,744,305 | A | 4/1998 | Fodor et al. |
| 7,727,733 | B2 | 6/2010 | Buhimschi et al. |
| 2005/0170444 | A1 | 8/2005 | Karumanchi et al. |
| 2009/0155827 | A1* | 6/2009 | Zeiher ............. G01N 33/74 435/15 |
| 2013/0136745 | A1 | 5/2013 | Toporsian |

FOREIGN PATENT DOCUMENTS

| | | | |
|---|---|---|---|
| EP | 1804836 B1 | 11/2010 | |
| WO | 2004/008946 A2 | 1/2004 | |
| WO | WO2005/017192 * | 2/2005 | ............... C12Q 1/00 |
| WO | WO2007/051069 * | 5/2007 | ............. G01N 33/50 |
| WO | 2008/034750 A1 | 3/2008 | |
| WO | WO2009/097579 * | 8/2009 | ............. G01N 33/68 |
| WO | 2011/143538 A1 | 11/2011 | |
| WO | 2013/068475 A1 | 5/2013 | |
| WO | 2014/001244 A1 | 1/2014 | |

OTHER PUBLICATIONS

Wang et al., The Journal of Maternal-Fetal and Neonatal Medicine, 2012: 25(8): 1447-1452 (Year: 2012).*
Seely et al., Circulation. 2014; 129: 1254-1261 (Year: 2014).*
Hamza et al., Archives of Gynecology and Obstetrics (2019) 299:1557-1566 (Year: 2019).*
Berg, Cynthia J. et al., "Pregnancy-Related Mortality in the United States, 1998 to 2005," Obstetrics & Gynecology, 2010, pp. 1302-1309, vol. 116, No. 6.
Brocklehurst, Peter et al., Antenatal care routine care for the healthy pregnant woman Clinical Guideline, National Collaborating Centre for Women's and Children's Health, 2008, 454 pps.
Brown, Mark A. et al., The Classification and Diagnosis of the Hypertensive Disorders of Pregnancy: Statement from the International Society for the Study of Hypertension in Pregnancy (ISSHP), Hypertension in Pregnancy, 2001, pp. ix-xiv, vol. 20, No. 1.
Chen, Yu, Novel Angiogenic Factors for Predicting Preeclampsia: sFlt-1, PIGF, and Soluble Endoglin, The Open Chemical Chemistry Journal, 2009, pp. 1-6, No. 2.
Duley, Lelia, "The Global Impact of Pre-eclampsia and Eclampsia," Seminars in Perinatology, 2009, pp. 130-137, vol. 33.
Gilstrap, Larry C. III and Ramin, Susan M., "Diagnosis and Management of Preeclampsia and Eclampsia," ACOG Practice Bulletin, 2002, 9 pages, No. 33.
Guideline of the German Society of Obstetrics and Gynecology: Diagnosis and therapy of hypertensive diseases in pregnancy, AWMF online, 2013, 37 pps., No. 015/018, Klasse S1.
Haram, Kjell et al., The HELLP syndrome: Clinical issues and management. A Review, BMC Pregnancy and Childbirth, 2009, 15 pps., vol. 9, No. 8.
International Search Report issued Mar. 26, 2015, in Application No. PCT/EP2015/051457, 4 pages.

(Continued)

*Primary Examiner* — Christina M Borgeest
(74) *Attorney, Agent, or Firm* — Taft Stettinius & Hollister LLP

(57) ABSTRACT

The present invention is directed to a method for predicting the risk of a female subject to develop postpartum HELLP syndrome, postpartum preeclampsia, or postpartum eclampsia. The method is based on the determination of the levels of i) sFlt-1 and PlGF, or ii) Endoglin and PlGF in a first sample obtained from said subject before delivery of baby, and a second sample of from said subject obtained after delivery of baby. Moreover, encompassed by the invention are devices and kits for carrying out the method of the present invention.

9 Claims, No Drawings

(56) References Cited

OTHER PUBLICATIONS

Kendall, Richard L. et al., Identification of a Natural Soluble Form of the Vascular Endothelial Growth Factor Receptor, FLT-1, and its Heterodimerization with KDR, Biochemical and Biophysical Research Communications, 1996, pp. 324-328, vol. 226.

Maglione, Domenico et al., Two alternative mRNAs coding for the angiogenic factor, placenta growth factor (PIGF), are transcribed from a single gene of chromosome 14, Oncogene, 1993, pp. 2333-2339, vol. 8.

Needleman, Saul B. and Wunsch, Christian D., A General Method Applicable to the Search for Similarities in the Amino Acid Sequence of Two Proteins, Journal of Molecular Biology, 1970, pp. 443-453, vol. 48.

Nolan, John P. and Sklar, Larry A., Suspension array technology: evolution of the flat-array paradigm, Trends in Biotechnology, 2002, pp. 9-12, vol. 20, No. 1.

Pearson, William R. and Lipman, David J., "Improved tools for biological sequence comparison", Proceedings of the National Academy of Sciences USA, 1988, pp. 2444-2448, vol. 85.

Pop-Trajkovic, Sonja et al., Postpartum HELLP syndrome—the case of lost battle, Upsala Journal of Medical Sciences, 2013, pp. 51-53, vol. 118, Issue 1.

Rana, Sarosh et al., "Sequential Changes in Antiangiogenic Factors in Early Pregnancy and Risk of Developing Preeclampsia," Hypertension, 2007, pp. 137-142, No. 50.

Reddy, Aparna et al., Maternal Circulating Levels of Activin A, Inhibin A, sFlt-1 and Endoglin at Parturition in Normal Pregnancy and Pre-Eclampsia, PLoS One, 2009, e4453, 9 pps., vol. 4, No. 2.

Richter, Mark M., Electrochemiluminescence (ECL), Chemical Reviews, 2004, pp. 3003-3036, vol. 104.

Sibai, Baha et al., Pre-eclampsia, Lancet, 2005, pp. 785-799, vol. 365, No. 9461.

Smith, Temple F. and Waterman, Michael S., Comparison of Biosequences, Advances in Applied Mathematics, 1981, pp. 482-489, vol. 2.

Sunderji, Shiraz et al., "Automated assays for sVEGF R1 and PIGF as an aid in the diagnosis of preterm preeclampsia: a prospective clinical study," American Journal of Obstetrics & Gynecology, 2010, pp. 40.e1-40.e7, vol. 202.

Verlohren, Stefan et al., "An Automated method for the determination of the sFlt-1/PIGF ratio in the assessment of preeclampsia," American Journal of Obstetrics & Gynecology, 2010, pp. 161.e1-161.e11, vol. 202.

Wang, Alice et al., Circulating anti-angiogenic factors during hypertensive pregnancy and increased risk of respiratory distress syndrome in preterm neonates, The Journal of Maternal-Fetal and Neonatal Medicine, 2012, pp. 1447-1452, vol. 25, No. 8.

Wikström, Anna-Karin et al., Early postpartum changes in circulating pro- and anti-angiogenic factors in early-onset and late-onset pre-eclampsia, Acta Obstetricia et Gynecologica, 2008, pp. 146-153, vol. 87, No. 2.

Prager et al., Unter Prapartaler Dexamethason-Therapie beim HELLP Syndrom, Z Geburtshilfe Neonatol 2013; 217: Po01_6 DOI: 10.1055/s-0033-1361384.

ACOG Practice Bulletin, Clinical Management Guidelines for Obstetrician—Gynecologists, No. 33, Jan. 2002.

Schiettecatte, Johann et al., "Multicenter evaluation of the first automated Elecsys sFlt-1 and PIGF assays in normal pregnancies and preeclampsia. Clinical biochemistry, 2010, vol. 43, No. 9, p. 768-770.

Powers, Robert W., Jeyabalan, Arun, Clifton, Rebecca G., et al. Soluble fms-Like tyrosine kinase 1 (sFlt1), endoglin and placental growth factor (PIGF) in preeclampsia among high risk pregnancies. PLoS one, 2010, vol. 5, No. 10, p. e13263.

\* cited by examiner

RATIOS OF sFlt-1 TO PlGF OR ENDOGLIN TO PlGF AS BIOMARKERS FOR PREECLAMPSIA RELATED ADVERSE OUTCOMES AFTER BIRTH

CROSS-REFERENCE TO RELATED APPLICATIONS

This application is a continuation of U.S. patent application Ser. No. 15/216,980 filed Jul. 22, 2016, which is a continuation of International Patent Application No. PCT/EP2015/051457 filed Jan. 26, 2015, and claims priority to EP 14152447.0 filed Jan. 24, 2014, the disclosures of which are hereby incorporated by reference in their entirety.

BACKGROUND

The present invention is directed to a method for predicting the risk of a female subject with an uneventful pregnancy to develop at least one preeclampsia related adverse outcome after delivery of baby. The method is based on the determination of the levels of i) sFlt-1 and PlGF, or ii) Endoglin and PlGF in a first sample obtained from said subject before delivery of baby, and a second sample of from said subject obtained after delivery of baby. Moreover, encompassed by the invention are devices and kits for carrying out the method of the present invention.

Pregnancy may be complicated in different ways. It is on one hand associated with pregnancy related mortality of the pregnant woman and, on the other hand, also associated with increased morbidity and mortality of the newborn. Maternal mortality at a rate of 14.5 per 100,000 live births, is more frequent in pregnant women above the age of 39 years and may be caused by hemorrhage, thrombotic pulmonary embolism, infections, cardiomyopathy and cardiovascular and noncardiovascular conditions as well as hypertensive disorders among which preeclampsia is the most frequent (Berg 2010, Obstetrics and Gynecology: 116: 1302-1309).

Preeclampsia complicates approximately 2 to 8 percent of all pregnancies and is a major contributor to maternal and fetal mortality worldwide (Duley 2009, Semin Perinatol: 33: 130-37). Preeclampsia usually occurs during pregnancy. However, it may also develop postpartum, i.e. after delivery of baby.

Preeclampsia is generally defined as pregnancy associated or induced hypertension. It is characterized by hypertension and proteinuria. Details are also found in the standard text books of medicine and the Guidelines of the various clinical societies, e.g., Brown M A, Lindheimer M D, de Swiet M, Van Assche A, Moutquin J M: The classification and diagnosis of the hypertensive disorders of pregnancy: statement from the International Society for the Study of Hypertension in Pregnancy (ISSHP). Hypertens Pregnancy 2001, 20:IX-XIV or ACOG Practice Bulletin, Clinical Management Guidelines for Obstetrician—Gynecologists, no.: 33, January 2002 or DGGG. S1-Leitlinie: Diagnostik und Therapie hypertensiver Schwangerschaftserkrankungen der Deutschen Gesellschaft für Gynäkologie und Geburtshilfe, AWMF online, AWMF Register Nummer 015/018, Klasse S1.

In addition to preeclampsia, there are further preeclampsia related adverse outcomes which may develop after childbirth, e.g. HELLP syndrome and eclampsia. All conditions are associated with adverse outcomes for the mother postpartum.

HELLP syndrome is a life-threatening obstetric complication and involves hemolytic anemia, elevated liver function tests (LFTs), and low platelet count. HELLP usually begins during the third trimester; however up to 30% of all patients develop this syndrome after parturition, typically within 48 hours. Unexpectedness, suddenness, and fulminant course of this syndrome are essential. In 20% of cases there maybe no evidence of pre-eclampsia before or during labour and all laboratory findings were normal. (Haram K, Svendsen E, Abildgaard U. The HELLP syndrome: clinical issues and management. A review. BMC Pregnancy and Childbirth 2009; 9(8). dx.doi.org/10.1186/1471-2393-9-8; Pop-Trajkovic et al. 2013 Uppsala Journal of Medical Sciences 118, 51-53).

Eclampsia is commonly defined as new onset of grand mal seizure activity and/or unexplained coma during pregnancy or postpartum in a woman with signs or symptoms of preeclampsia. It typically occurs during or after the 20th week of gestation or in the postpartum period after childbirth and delivery of the placenta.

There is a high unmet medical need to identify women at risk of developing postpartum HELLP syndrome, eclampsia, or preeclampsia immediately after birth.

Placental growth factor (PlGF), soluble Endoglin und soluble fms-like tyrosine kinase 1 (sFlt-1) have been described as marker for diagnosing and prediction preeclampsia during pregnancy (see e.g. WO2004/008946, WO2008/034750; Rana, 2007, Hypertension 50:137-142). Ratios of sFlt-1 and PlGF or Endoglin and PlGF have been reported as diagnostic or prognostic parameters for preeclampsia in pregnant women before delivery.

It is known in the literature that angiogenic factors and anti-angiogenic factors rapidly decline after delivery in healthy women as well as in preeclamptic women.

Wikström et al. examined the concentration levels of sFIT-1 and PlGF before and after delivery in preeclamptic women and controls and found a rapid decline for both markers in all groups (Acta Obstericia et Gynecologia, 2008; 87: 146-153). However, women showing complications of preeclampsia postpartum were not included in the study.

Reddy et al. found that the concentration levels of sFlt-1 (and activin A, but not soluble Endoglin) increase during labour in preeclamptic women compared to normal control women (PLOS ONE, 2009, 4(2), e4453). They found that in both groups sFlt-1 levels decline within 24 hours. Women showing postpartum complications were not included in the study.

WO 2013/068475 describes a method for diagnosing pregnant women at risk for developing preeclampsia (between about week 15 and about week 34 of gestation) within a short period of time by two measurements of the Ratio (sFlt-1/PlGF). Women are at risk if ratio 2 to ratio is increased by a factor of at least about 3.

WO 2014/001244 describes a method for diagnosing whether a pregnant women is not at risk for developing preeclampsia (eclampsia and/or HELLP syndrome) within a short period of time (1-2 weeks); the pregnant subject is between about week 20 and about week 40 of gestation.

Prager et al. 2013 monitored the ratios of sFlt-1/PlGF in pregnant women with onset of HELLP syndrome before delivery under cortison therapy. Women showing postpartum HELLP syndrome were not included in the study (Prager, R; Eckart, A; Meint, P; Seelbach-Göbel, B: Verhalten der Angiogenesefaktoren (PlGF und sFlt-1) unter präpartaler Dexamethason-Therapie beim HELLP-Syndrom, Z Geburtshilfe Neonatol 2013; 217: Po01_6 DOI: 10.1055/s-0033-1361384).

Early diagnosis of postpartum complications is important because the morbidity and mortality rates associated with these complications that have been reported are high. For example, postpartum preeclampsia requires prompt treatment. Left untreated, postpartum preeclampsia can result in seizures and other serious complications. Thus, a reliable assay for identifying a subject who is at risk of developing postpartum HELLP syndrome, postpartum eclampsia and postpartum preeclampsia is not yet available but nevertheless highly desired.

SUMMARY

The technical problem underlying the present invention can be seen as the provision of means and methods for complying with the aforementioned needs. The technical problem is solved by the embodiments characterized in the claims and herein below.

Advantageously, it has been found in the context of the studies underlying the present invention that the sFlt-1/PlGF or Endoglin/PlGF ratio in a female subject with an uneventful pregnancy, serve as biomarker for predicting the risk of said subject of developing a preeclampsia related adverse outcome after delivery of baby, in particular of developing postpartum preeclampsia, postpartum eclampsia, and/or postpartum HELLP syndrome. Remarkably, an increase of the ratio of sFlt-1/PlGF or Endoglin/PlGF obtained after delivery of baby as compared to a sample obtained before delivery of baby was indicative for a risk of developing a preeclampsia related adverse outcome after delivery of baby, whereas a decrease of the ratio of sFlt-1/PlGF or Endoglin/PlGF was indicative for a subject who is not at risk of developing a preeclampsia related adverse outcome after delivery of baby.

Thanks to the present invention, it is possible to more reliably assess the risk of developing at least one preeclampsia related adverse outcome after delivery of baby, based on a reliable indicator. Moreover, the time consuming, expensive and cumbersome diagnostic measures can be avoided when applying the method of the invention and suitable supportive measures can be initiated. Health care management shall greatly benefit from the method of the present invention.

Accordingly, the present invention relates to a method for predicting the risk of a female subject to develop at least one preeclampsia related adverse outcome after delivery of baby (and thus to suffer from at least one preeclampsia related adverse outcome after delivery of baby), said method comprising the steps of
a) measuring in a first sample obtained from a female subject with an uneventful pregnancy before delivery of baby
   i) the level of the biomarker sFlt-1 (soluble fms-like tyrosine kinase-1) or the level of the biomarker Endoglin, and
   ii) the level of the biomarker PlGF (Placental Growth Factor),
b) calculating a first ratio of the levels of the biomarkers as measured in step a),
c) measuring in a second sample obtained from said female subject after delivery of baby the levels of the biomarkers as measured in step a),
d) calculating a second ratio of the levels measured in step c), and
e) comparing the second ratio to the first ratio.

In an embodiment, step e) of comparing the second ratio to the first ratio is carried out by calculating a ratio of the second ratio to the first ratio (or vice versa).

Preferably, the risk of the female subject to develop at least one preeclampsia related adverse outcome after delivery of baby is predicted based on the results of the comparison step carried out in step (e). Accordingly, the aforementioned method may further comprise the further step of predicting (or providing a prediction of) the risk of the female subject to develop at least one preeclampsia related adverse outcome after delivery of baby based on the results of the comparison step.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, the measurement steps, the calculation steps and the comparison step may in total or in part be assisted by automation, e.g., by a suitable robotic and sensory equipment for the measurement, a computer-implemented calculation algorithm on a data processing device in the calculation steps, or comparison and/or diagnosis algorithm on a data processing device in the comparison step.

DETAILED DESCRIPTION

In accordance with the present invention, the risk of the female subject to develop and, thus, to suffer from at least one preeclampsia related adverse outcome after delivery of baby shall be predicted. Preeclampsia related adverse outcomes that develop after delivery of baby are well known by the skilled person. As used herein, the term preferably refers to a preeclampsia related adverse outcome which develops after pregnancy. Preferably, the at least one preeclampsia related adverse outcome after delivery of baby is selected from the group consisting of postpartum HELLP syndrome, postpartum preeclampsia, and postpartum eclampsia, postpartum cerebral hemorrhage, postpartum renal failure, in particular postpartum acute renal failure, postpartum pulmonary edema, in particular acute postpartum pulmonary edema, postpartum cerebral edema, and postpartum liver rupture, disseminated intravascular coagulation (DIC) and postpartum maternal death. More preferably, at least one preeclampsia related adverse outcome after delivery of baby is selected from the group consisting of postpartum HELLP syndrome, postpartum preeclampsia, and postpartum eclampsia. Accordingly, it is preferably predicted whether the female subject is a risk of developing postpartum HELLP syndrome, postpartum preeclampsia, and/or postpartum eclampsia.

The term "at least one preeclampsia related adverse outcome" refers to one preeclampsia related adverse outcome or more than one, i.e. two or three (or even more) preeclampsia related outcomes (since e.g. eclampsia usually follows preeclampsia).

The term "preeclampsia" as used herein refers to a medical condition which is characterized by hypertension and proteinuria. Preeclampsia can occur in pregnant female subjects before and after delivery of baby, i.e. before and after childbirth. In the context of the present invention, the risk of a subject to suffer from preeclampsia after delivery of a baby shall be predicted, rather than to suffer from preeclampsia during pregnancy. Most cases of postpartum preeclampsia develop within 48 hours after childbirth. However, postpartum preeclampsia sometimes develops up to four to six weeks after childbirth. This is known as late postpartum preeclampsia. Preferably, the pregnancy-induced hypertension is identified to be present in a subject by two blood pressure measurements of 140 mmHg (systolic) to 90 mmHg (diastolic) or more, wherein said two measurements have been made at least 6 hours apart. Proteinuria is, preferably, identified to be present by 300 mg/dL protein or more, in particular, in a 24-hour urine sample. Also preferably, proteinuria is identified by protein dipstick analysis (if ≥2+), or if ≥30 mg/dL protein in present in a spot urine sample, or protein/creatinine ratio is ≥30 mg protein/mmol creatinine in spot urine.

Preeclampsia may progress to eclampsia, a life-threatening disorder characterized by the appearance of tonicclonic seizures or coma conditions. Symptoms associated with severe preeclampsia are oligouria of less than 500 ml within 24 hours, cerebral or visual disturbance, pulmonary edema or cyanosis, epigastric- or right upper quadrant-pain, impaired liver function, thrombocytopenia.

The term "HELLP syndrome" is well known in the art. HELLP syndrome is a life-threatening obstetric complication usually considered complication of preeclampsia. Both conditions usually occur during the later stages of pregnancy, or after delivery of baby. In the context of the present invention, the risk of a female subject to suffer from HELLP syndrome after delivery shall be predicted. The HELLP syndrome is associated with a high risk of adverse outcomes such as renal failure, subcapsular hepatic hematoma, recurrent preeclampsia, or even death. "HELLP" is an abbreviation of the three main features of the syndrome: Hemolysis, Elevated Liver enzymes, and Low Platelet count. HELLP syndrome can be difficult to diagnose due to the variability of symptoms among patients (frequently patients have no symptoms other than general abdominal pain), and early diagnosis is key in reducing morbidity. If not treated in a timely manner, patients can become critically ill or die due to liver rupture/hemorrhage or cerebral edema. In a patient with possible HELLP syndrome, a batch of blood tests is performed: a full blood count, a coagulation panel, liver enzymes, electrolytes, and renal function studies. Often, fibrin degradation product (FDP) levels are determined, which can be elevated. Lactate dehydrogenase is a marker of hemolysis and is elevated (>600 U/liter). Proteinuria is present but can be mild.

Further details of preeclampsia and the accompanying symptoms as well as the follow up diseases such as HELLP syndrome or eclampsia are to be found in standard text books of medicine or Guidelines of the relevant medical societies. Details can be found, e.g., in ACOG Practice Bulletin, Clinical Management Guidelines for Obstetrician—Gynecologists, no.: 33, January 2002 or Haram K, Svendsen E, Abildgaard U. The HELLP syndrome: clinical issues and management. A review. BMC Pregnancy and Childbirth 2009; 9(8). dx.doi.org/10.1186/1471-2393-9-8 or DGGG. S1-Leitlinie: Diagnostik und Therapie hypertensiver Schwangerschaftserkrankun-gen der Deutschen Gesellschaft für Gynäkologie und Geburtshilfe, see citation above.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject. The subject according to the present invention shall be a female subject. The female subject shall be pregnant at the time at which the first sample is obtained. However, the second sample shall be obtained after delivery of baby. The terms "subject" and "patient" may be used interchangeably herein.

Preferably, the female subject shall be a subject with an uneventful pregnancy. The term "uneventful pregnancy" is well understood by the skilled person. In particular, it is envisaged that a subject with an uneventful pregnancy did not exhibit pre-eclampsia (in particular severe preeclampsia), eclampsia, and/or a HELLP syndrome during pregnancy (i.e. during the present pregnancy). Accordingly, the subject with an uneventful pregnancy preferably did not suffer from pre-eclampsia (in particular severe preeclampsia), eclampsia, and/or the HELLP syndrome before delivery of baby (in particular during the present pregnancy). In particular, it is envisaged that the subject did not suffer from pre-eclampsia (in particular severe preeclampsia), eclampsia, and the HELLP syndrome before delivery of baby.

Thus, at the time at which the first sample is obtained, the subject according to the present invention, preferably, shall preferably exhibit no clinical diagnosis of preeclampsia, eclampsia, and/or the HELLP syndrome before delivery. However, the subject according to the present invention may exhibit at least one symptom selected from the group consisting of epigastric pain, headache, visual disturbance, hypertension and edema and may, thus, suspected to be at risk of developing (and thus to suffer from) at least one preeclampsia related adverse outcome after delivery of baby, in particular of developing a postpartum HELLP syndrome, postpartum preeclampsia, and/or postpartum eclampsia. In an embodiment, the subject exhibits said at least one symptom shortly before delivery of baby, in particular the subject exhibits said at least one symptom at the time at which the first sample is obtained.

Further, it is envisaged that the subject with an uneventful pregnancy suffered from mild preeclampsia before delivery baby, i.e. in the present pregnancy. In this case, the risk refers to developing at least one severe preeclampsia related adverse outcome after delivery of baby. Preferably, the severe preeclampsia related adverse outcome is selected from postpartum HELLP syndrome, postpartum eclampsia and postpartum severe preeclampsia. The terms "mild preeclampsia" and "severe preeclampsia" are well known in the art. The term "mild preeclampsia" preferably refers to the of hypertension (in particular of a blood pressure ≥140/90 mm Hg) on 2 occasions, at least 6 hours apart, but without evidence of end-organ damage, in a woman who was normotensive before 20 weeks' gestation. The term "severe preeclampsia" refers to preeclampsia with at least one of the following symptoms, systolic blood pressure of 160 mm Hg or higher or diastolic blood pressure of 110 mm Hg or higher on 2 occasions at least 6 hours apart, proteinuria of more than 5 g in a 24-hour collection or more than 3+ on 2 random urine samples collected at least 4 hours apart, Oliguria (<400 mL in 24 hours), persistent headaches, epigastric pain and/or impaired liver function and thrombocytopenia. For a definition of the terms, see e.g. Sibai et al. Lancet. 2005 Feb. 26-Mar. 4; 365(9461):785-99. which herewith is incorporated by reference with respect to its entire disclosure content.

Also preferably, the subject may be a risk person for developing at least one preeclampsia related adverse outcome after delivery of baby, in particular of postpartum HELLP syndrome, postpartum preeclampsia, and/or postpartum eclampsia. A risk person preferably is a female subject being older than 40 years and/or a female subject in the first pregnancy, have a family history of pre-eclampsia (e.g., pre-eclampsia in a mother or sister), have a prior history of pre-eclampsia in previous pregnancy or after delivery of a previous baby, have a body mass index at or above 35 kg/m² at first contact, have a multiple pregnancy or pre-existing vascular disease such as hypertension or diabetes, e.g. as described in the NICE (National Institute for Health and Care Excellence)) Antenatal Care guideline CG62, March 2008.

The delivery technique may be any technique deemed appropriate. Preferably, the delivery technique includes one of a non-induced vaginal birth, a cesarean section, and a drug-induced labor. In preferred embodiment, a single baby is delivered. However, it is also envisaged that more than one baby is delivered. Preferably, the baby is apparently healthy after delivery.

In accordance with the method of the present invention, the risk of female subject to develop at least one preeclampsia related adverse outcome after delivery of baby, in particular postpartum HELLP syndrome, postpartum preeclampsia, and/or postpartum eclampsia shall be predicted, and, thus, the risk of a said subject to suffer from said adverse outcome. Preferably, it is predicted whether said adverse outcome develops immediately after delivery of baby. The term "immediately after delivery of baby" in connection with said adverse outcome, in particular with postpartum HELLP syndrome, postpartum preeclampsia, and/or postpartum eclampsia is well understood by the skilled person. Preferably, the risk is predicted to develop at least one preeclampsia related adverse outcome within two weeks, more preferably within seven days, even more preferably within 72 hours, or, most preferably, within 48 hours after delivery of baby. Preferably, the subject does not suffer from at least one preeclampsia related adverse outcome, in particular postpartum HELLP syndrome, postpartum preeclampsia and/or postpartum eclampsia at the time at which the second sample is obtained.

The term "predicting the risk" as used herein, preferably, refers to assessing the probability according to which at least one preeclampsia related adverse outcome will develop in a subject after delivery of baby or not. More preferably, the risk/probability of developing (and thus of suffering from) at least one preeclampsia related adverse outcome within a certain time window after delivery of baby is predicted. As set forth above, the predictive window, preferably, is an interval at two weeks, at seven days, of 72 hours, 48 hours, or any intermitting time range after delivery of baby. In a particular preferred embodiment of the present invention, the predictive window, preferably, is an interval of 48 hours. Preferably, said the predictive window is calculated from the delivery of baby. Also preferably, said predictive window is calculated from the time point at which the second sample has been obtained.

As will be understood by those skilled in the art, such a prediction is usually not intended to be correct for 100% of the subjects. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001. Preferably, the probability envisaged by the present invention allows that the prediction of an increased, normal or decreased risk will be correct for at least 60%, at least 70%, at least 80%, or at least 90% of the subjects of a given cohort or population. The term, preferably, relates to predicting whether a subject is at elevated risk or reduced risk as compared to the average risk for developing at least one preeclampsia related adverse outcome after delivery of baby in a population of female subjects immediately after delivery of baby.

The term "predicting the risk of developing at least one preeclampsia related adverse outcome after delivery of baby" as used herein means that the subject to be analyzed by the method of the present invention is allocated either into the group of subjects being at risk of developing said at least one adverse outcome, or into the group of subjects being not at risk of developing at least one preeclampsia related adverse outcome. A risk of developing said at least one adverse outcome as referred to in accordance with the present invention, preferably, means that the risk of developing said at least one adverse outcome is elevated (within the predictive window). Preferably, said risk is elevated as compared to the average risk in a cohort of female subjects immediately after delivery of baby (i.e. a group of such subjects). If a subject is not at risk of developing said a preeclampsia related adverse outcome as referred to in accordance with the present invention, preferably, the risk of developing said adverse outcome shall be reduced (within the predictive window). Preferably, said risk is reduced as compared to the average risk in a cohort of female subjects immediately after delivery of baby. A subject who is at risk of developing said at least one adverse outcome preferably has a risk of 80% or larger, or, more preferably of 60% or larger of developing said at least one adverse outcome, preferably, immediately after delivery of baby. A subject who is at not at risk of developing a preeclampsia related adverse outcome preferably has a risk of lower than 20%, more preferably of lower than, 10% or lower, or more preferably of 5% or lower of developing said at least one adverse outcome, preferably, immediately after delivery of baby.

In accordance with the present invention, a risk prediction may be provided. The phrase "providing a prediction" as used herein refers to using the information or data generated relating to first and second ratio in a sample of a patient to predict the risk of the subject to develop at least one preeclampsia related adverse outcome after delivery of baby. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the level of the marker in the sample. Likewise, biopsies may also be subjected to post-collection preparative and storage techniques, e.g., fixation.

In an embodiment the sample is a blood, plasma or, in particular, a serum sample. Preferably, the sample is a venous blood, venous serum or venous plasma sample derived from the female subject. Also preferably, the sample is a urine sample.

In accordance with the present invention, it is envisaged to measure the level of a biomarker as referred to herein in a first and a second sample from the female subject. The first sample shall have been obtained from the female subject before delivery of baby, in particular immediately before delivery of baby. Thus, the first sample, preferably, shall have been obtained within two weeks or one week, more preferably, within three days, even more preferably within 48 hours, or most preferably within 24 hours before delivery of baby. Further, it is envisaged to obtain the first sample within 12 hours before delivery of baby.

The "second sample" is, preferably, understood as a sample which is obtained in order to reflect a change of the second ratio as compared to the first ratio in the first sample. The second sample shall be obtained after the first sample. In particular, the second sample shall be obtained after delivery of baby. Preferably, the second sample has been obtained within 72 hours or within 48 hours after delivery of baby, more preferably, within 24 hours after delivery of baby, even more preferably within 16 hours, and most preferably within 12 hours after delivery of baby.

Preferably, the second sample is not obtained too early after the first sample (in order to observe a sufficiently significant change to allow the risk prediction). Thus, the "second sample" is preferably obtained not earlier than 10 hours, more preferably, not earlier than 8 hours, or most preferably not earlier than 6 hours after the first sample. Thus, there should be an interval of preferably at least 10 hours, more preferably, of at least 8 hours and most preferably at least 6 hours between obtaining the first and the second sample.

Also preferably, it is envisaged that the first sample is obtained not earlier than three hours before delivery of baby and that the second sample is obtained not earlier than three hours after delivery of baby. Also, the first sample may be obtained not earlier than five hours before delivery of baby and the second sample may be obtained not earlier than five hours after delivery of baby.

The term "delivery" in connection with childbirth is well understood by the skilled person. It is the culmination of a period of pregnancy with the expulsion of one or more newborn infants from a woman's uterus. As used herein, the expression "delivery of baby" preferably refers to the birth of the baby. More preferably, the delivery of baby is the time point at which the fetus is expelled from the subject's uterus. Most preferably, the delivery of baby is the time point at which the baby starts breathing. It is also envisaged that the delivery of baby is the time point at which the placenta is delivered.

In an embodiment of the present invention, there are no maternal or fetal complications during childbirth.

It is to be understood that the first and the second sample are the same kind of sample. E.g., if the first sample is a serum sample the second sample shall be a serum sample as well.

The term "measuring" the level of a marker as referred to herein refers to the quantification of the biomarker, e.g. to determining the level of the biomarker in the sample, employing appropriate methods of detection described elsewhere herein.

In an embodiment, the level of the at least one biomarker is measured by contacting the sample with a detection agent that specifically binds to the respective marker, thereby forming a complex between the agent and said marker, detecting the level of complex formed, and thereby measuring the level of said marker.

The biomarkers as referred to herein can be detected using methods generally known in the art. Methods of detection generally encompass methods to quantify the level of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used immunoassays.

Methods for measuring electrochemiluminescent phenomena are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

Biomarkers can also be detected by generally known methods including magnetic resonance spectroscopy (NMR spectroscopy), Gas chromatography-mass spectrometry (GC-MS), Liquid chromatography-mass spectrometry (LC-MS), High and ultra-HPLC HPLC such as reverse phase HPLC, for example, ion-pairing HPLC with dual UV-wavelength detection, capillary electrophoresis with laser-induced fluorescence detection, anion exchange chromatography and fluorescent detection, thin layer chromatography.

Preferably, measuring the level of a biomarker as referred to herein comprises the steps of (a) contacting a cell capable of eliciting a cellular response the intensity of which is indicative of the level of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the level of the peptide or polypeptide.

Also preferably, measuring the level of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Measuring the level of a peptide or polypeptide may, preferably, comprises the steps of (a) contacting the peptide with a specific binding agent, (b) (optionally) removing non-bound binding agent, (c) measuring the level of bound binding agent, i.e. the complex of the binding agent formed in step (a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound binding agent, i.e. the binding agent or the binding agent/peptide complex, will generate an intensity signal. Binding according to the present invention includes both covalent and non-covalent binding. A binding agent according to the present invention can be any compound, e.g., a peptide, polypeptide, nucleic acid, or small molecule, binding to the peptide or polypeptide described herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such binding agents are well-known in the art. For example, identification and production of suitable antibodies or aptamers is also offered by commercial suppliers. The person skilled in the art is familiar with methods to develop derivatives of such binding agents with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the binding agent or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the binding agent can be measured by any method known in the art. Preferably, said method is semi-quantitative or quantitative. Further suitable techniques for the determination of a polypeptide or peptide are described in the following.

Binding of a binding agent may be measured directly, e.g. by NMR or surface plasmon resonance. Measurement of the binding of a binding agent, according to preferred embodiments, is performed by an analyzer unit of a system disclosed herein. Thereafter, a level of the measured binding may be calculated by a computing device of a system disclosed herein. If the binding agent also serves as a substrate of an enzymatic activity of the peptide or polypeptide of interest, an enzymatic reaction product may be measured (e.g. the level of a protease can be measured by measuring the level of cleaved substrate, e.g. on a Western Blot). Alternatively, the binding agent may exhibit enzymatic properties itself and the "binding agent/peptide or polypeptide" complex or the binding agent which was bound by the peptide or polypeptide, respectively, may be contacted with a suitable substrate allowing detection by the generation of an intensity signal. For measurement of enzymatic reaction products, preferably the level of substrate is saturating. The substrate may also be labeled with a detectable label prior to the reaction. Preferably, the sample is contacted with the substrate for an adequate period of time. An adequate period of time refers to the time necessary for a detectable, preferably measurable, level of product to be produced. Instead of measuring the level of product, the time necessary for appearance of a given (e.g. detectable) level of product can be measured. Third, the binding agent may be coupled covalently or non-covalently to a label allowing detection and measurement of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. The use of secondary, tertiary or even higher order binding agents is often used to increase the signal. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Gluta-thion-S-Transferase, FLAG, GFP, myctag, influenza A virus hae-magglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as readymade stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The level of a peptide or polypeptide may be, also preferably, determined as follows: (a) contacting a solid support comprising a binding agent for the peptide or polypeptide as specified above with a sample comprising the peptide or polypeptide and (b) measuring the level peptide or polypeptide which is bound to the support. The binding agent, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The binding agent or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said binding agent are well known and include, but are not limited to ionic, hydrophobic, covalent interactions and the like. It is also contemplated to use "suspension arrays" as arrays according to the present invention (No-lan 2002, Trends Biotechnol. 20(1):9-12). In such suspension arrays, the carrier, e.g. a mi-crobead or microsphere, is present in suspension. The array consists of different microbeads or microspheres, possibly labeled, carrying different binding agents. Methods of producing such arrays, for example based on solid-phase chemistry and photo-labile protective groups, are generally known (U.S. Pat. No. 5,744,305).

In an embodiment of the present invention, the levels of the biomarkers as referred to herein are measured by using the assays described in the Examples section.

In another embodiment of the method of the present invention, the measurement in step a) (or in steps a) and c)) may be carried out by an analyzer unit, in particular by an analyzer unit as defined elsewhere herein.

The term "binding agent" refers to a molecule that comprises a binding moiety which specifically binds the corresponding to the respective biomarker. Examples of "binding agent" are a aptamer, antibody, antibody fragment, peptide, peptide nucleic acid (PNA) or chemical compound.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

Examples of "binding agents" or "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Preferably, the antibody is a polyclonal antibody. More preferably, the antibody is a monoclonal antibody.

Another binding agent that can be applied, in an aspect, may be an aptamere which specifically binds to the at least one marker in the sample. The term "specific binding" or "specifically binds", when referring to a nucleic acid aptamer as a binding agent, refers to a binding reaction wherein a nucleic acid aptamer binds to the corresponding target molecule with an affinity in the low nM to pM range.

In yet an aspect the, sample is removed from the complex formed between the binding agent and the at least one marker prior to the measurement of the level of formed complex. Accordingly, in an aspect, the binding agent may be immobilized on a solid support. In yet an aspect, the sample can be removed from the formed complex on the solid support by applying a washing solution. The formed complex shall be proportional to the level of the at least one marker present in the sample. It will be understood that the specificity and/or sensitivity of the binding agent to be applied defines the degree of proportion of at least one marker comprised in the sample which is capable of being specifically bound. Further details on how the determination can be carried out are also found elsewhere herein. The level of formed complex shall be transformed into a level of at least one marker reflecting the level indeed present in the sample. Such a level, in an aspect, may be essentially the level present in the sample or may be, in another aspect, an level which is a certain proportion thereof due to the relationship between the formed complex and the level present in the original sample.

The term "sFlt-1" as used herein refers to a polypeptide which is a soluble form of the fms-like tyrosine kinase 1. The polypeptide is also referred to as soluble VEGF receptor 1 (sVEGF R1) in the art (see, e.g., Sunderji 2010, Am J Obstet Gynecol 202: 40e1-7). It was identified in conditioned culture medium of human umbilical vein endothelial cells. The endogenous sFlt-1 receptor is chromatographically and immunologically similar to recombinant human sFlt-1 and binds VEGF with a comparable high affinity. Human sFlt-1 is shown to form a VEGF-stabilized complex with the extracellular domain of KDR/Flk-1 in vitro. Preferably, sFlt-1 refers to human sFlt-1 as describe in Kendall 1996, Biochem Biophs Res Commun 226(2): 324-328; for amino acid sequences, see, e.g., also Genebank accession numbers P17948, GI: 125361 for human and BAA24499.1, GI: 2809071 for mouse sFlt-1 (Genbank is available from the NCBI, USA under ncbi.nlm.nih.gov/entrez). The term also encompasses variants of the aforementioned human sFlt-1 polypeptides. Such variants have at least the same essential biological and immunological properties as the aforementioned sFlt-1 polypeptide. In particular, they share the same essential biological and immunological properties if they are detectable by the same specific assays referred to in this specification, e.g., by ELISA assays using polyclonal or monoclonal antibodies specifically recognizing the said sFlt-1 polypeptides. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific sFlt-1 polypeptide, preferably over the entire length of the human sFlt-1, respectively. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Variants referred to above may be allelic variants or any other species specific homologs, paralogs, or orthologs. Moreover, the variants referred to herein include fragments or subunits of the specific sFlt-1 polypeptides or the aforementioned types of variants as long as these fragments have the essential immunological and biological properties as referred to above. Such fragments may be, e.g., degradation products of the sFlt-1 polypeptides. Variants are deemed to share the same essential biological and immunological properties if they are detectable by the same specific assays referred to in this specification, e.g., by ELISA assays using polyclonal or monoclonal antibodies specifically recognizing the said sFlt-1 polypeptides. A preferred assay is described in the accompanying Examples. Further included are variants which differ due to posttranslational modifications such as phosphorylation or myristylation. sFlt-1 may be detected in bound or free form or as total sFlt1 level in a sample.

The term "Endoglin" as used herein refers to a polypeptide having a molecular weight of 180 kDa non-reduced, 95 kDa after reduction and 66 kDa in its reduced and N-deglycosylated form. Preferably, the term "Endoglin" refers to soluble Endoglin. The polypeptide is capable of forming dimers and binds to TGF-ß and TGF-ß receptors. Preferably, Endoglin refers to human Endoglin. More preferably, human Endoglin has an amino acid sequence as shown in Genebank accession number AAC63386.1, GI: 3201489. Two Endoglin isoforms, S-Endoglin and L-Endoglin have been described. L-Endoglin consists of total of 633 amino acids with a cytoplasmic tail of 47 amino acids while S-Endoglin consists of 600 amino acids with a cytoplasmic tail of 14 amino acids. Preferably, Endoglin as used herein is soluble Endoglin. Soluble Endoglin as referred to herein is preferably described in EP 1 804 836 B1. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific Endoglin. Variants may be allelic variants, splice variants or any other species specific homologs, paralogs, or orthologs. Moreover, the variants referred to herein include fragments of the specific Endoglin or the aforementioned types of variants as long as these fragments have the essential immunological and biological properties as referred to above. Such fragments may be, e.g., degradation products of Endoglin. Variants are deemed to share the same essential biological and immunological properties if they are detectable by the same specific assays referred to in this specification, e.g., by ELISA assays using polyclonal or monoclonal antibodies specifically recognizing the said Endoglin polypeptides. A preferred assay is described in the accompanying Examples. Further included are variants which differ due to posttranslational modifications such as phosphorylation or myristylation. Endoglin may be detected in bound or free form or as total Endoglin level in a sample.

The term "PlGF (Placental Growth Factor)" as used herein, preferably, refers to a placenta-derived growth factor which is a polypeptide having 149 amino acids in length and being highly homologous to the platelet-derived growth factor-like region of human vascular endothelial growth factor (VEGF). Like VEGF, PlGF has angiogenic activity in vitro and in vivo. For example, biochemical and functional characterization of PlGF derived from transfected COS-1 cells revealed that it is a glycosylated dimeric secreted protein which is able to stimulate endothelial cell growth in vitro (Maglione 1993, Oncogene 8(4):925-31). Preferably, PlGF refers to human PlGF, more preferably, to human PlGF having an amino acid sequence as shown in Genebank accession number P49763, GI: 17380553. The term encompasses variants of said specific human PlGF. Such variants have at least the same essential biological and immunological properties as the specific PlGF polypeptide. Variants are deemed to share the same essential biological and immunological properties if they are detectable by the same specific assays referred to in this specification, e.g., by ELISA assays using polyclonal or monoclonal antibodies specifically recognizing the said PlGF polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific PlGF polypeptides. The degree of identity between two amino acid sequences can be determined by algorithms well known in the art and described elsewhere herein. Variants referred to above may be allelic variants or any other species specific homologs, paralogs, or orthologs. Moreover, the variants referred to herein include fragments of the specific PlGF polypeptides or the aforementioned types of variants as long as these fragments have the essential immunological and biological properties as referred to above. Such fragments may be, e.g., degradation products or splice variants of the PlGF polypeptides. Further included are variants which differ due to posttranslational modifications such as phosphorylation or myristylation. PlGF may be detected in bound or free form or as total PlGF level in a sample.

The term "level" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the ratio of the levels of the biomarkers as referred to herein (first ratio) in the first sample from the subject with the ratio of the levels of said biomarkers (second ratio) in the second sample from the subject. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the (first) ratio in the first sample from the subject and the value of the (second) ratio in the second sample can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined ratio in the second sample may be compared to a value of the ratio in the first sample which is stored in a database by a computer program. The computer program may further evaluate the result of the comparison, i.e. automatically provide the desired assessment in a suitable output format. For a computer assisted comparison, the value of the determined ratio in the second sample may be compared to the value of the ratio in the first sample which is stored in a database by a computer program. The computer program may further evaluate the result of the comparison, i.e. automatically provides the desired assessment in a suitable output format.

The term "calculating a first ratio" or "calculating a second ratio" as referred to herein relates to calculating a ratio of the level of sFlt-1 or Endoglin and the level of PlGF by dividing the said level or by carrying out any other comparable mathematical calculation which puts into a relation the level of sFlt-1 or Endoglin towards the level of PlGF. Preferably, the level of sFlt-1 or Endoglin is divided by the level of PlGF in order to calculate the ratio (thus, the ratio of the level of sFlt-1 or Endoglin to the level of PlGF is calculated). Also preferably, the level of PlGF is divided by the level of sFlt-1 or Endoglin in order to calculate the ratio (thus, the ratio of the level of PlGF to the level of sFlt-1 or Endoglin is calculated). The calculation is carried out for the respective levels determined in the said first and the said second sample separately yielding the first and the second ratio, respectively. The calculations may be carried at the same time, or at different times.

If the method comprises the comparison of the second ratio to the first ratio, preferably, the following applies:

In an embodiment, the first and the second ratio are the ratios of sFlt-1 to PlGF, or of Endoglin to PlGF. Preferably, an increase of the second ratio (or an essentially unchanged second ratio) as compared to the first ratio is indicative for a subject who is at risk of developing at least one preeclampsia related adverse outcome after delivery of baby, and/or a decrease of the second ratio as compared to the first ratio is indicative for a subject who is not at risk of developing a preeclampsia related adverse outcome after delivery of baby. Also preferably, the subject is at risk of developing at least one preeclampsia related adverse outcome after delivery of baby, if the second ratio is increased as compared to the first ratio, or if the second ratio is essentially the same as the first ratio, whereas the subject is not at risk of developing a preeclampsia related adverse outcome after delivery of baby, if the second ratio is decreased as compared to the first ratio.

In another embodiment, the first and the second ratio are the ratios of PlGF to sFlt-1, or of PlGF to Endoglin. Preferably, a decrease of the second ratio (or an essentially unchanged second ratio) as compared to the first ratio is indicative for a subject who is at risk of developing at least one preeclampsia related adverse outcome after delivery of baby, and/or an increase of the second ratio as compared to the first ratio is indicative for a subject who is not at risk of developing a preeclampsia related adverse outcome after delivery of baby. Also preferably, the subject is at risk of developing at least one preeclampsia related adverse outcome after delivery of baby, if the second ratio is decreased as compared to the first ratio, or if the second ratio is essentially the same as the first ratio, whereas the subject is not at risk of developing a preeclampsia related adverse outcome after delivery of baby, if the second ratio is increased as compared to the first ratio.

The term "essentially unchanged" is well known in the art and understood by the skilled person who is experienced in the field of diagnostics. The term refers to minor changes of the second ratio as compared to the first ratio, e.g. of less than 3 or 7%. In an embodiment the term refers to an unchanged ratio.

If step e) of comparing the second ratio to the first ratio is carried out by calculating a ratio of the second ratio to the first ratio (or vice versa), preferably the following applies:

If first and the second ratio are the ratios of sFlt-1 to PlGF, or of Endoglin to PlGF, the following applies: Preferably, a ratio which is equal or larger than 1 is indicative for a subject who is at risk of developing at least one preeclampsia related adverse outcome after delivery of baby, whereas a ratio which lower than 1 is indicative for a subject who is not at risk of developing a preeclampsia related adverse outcome after delivery of baby.

If first and the second ratio are the ratios of PlGF to sFlt-1, or of PlGF to Endoglin the following applies: Preferably, a ratio which is equal or lower than 1 is indicative for a subject who is at risk of developing at least one preeclampsia related adverse outcome after delivery of baby, whereas a ratio which larger than 1 is indicative for a subject who is not at risk of developing a preeclampsia related adverse outcome after delivery of baby.

In accordance with the present invention, the terms "increase" and "decrease" preferably refer to a statistically significant increase and decrease respectively. Particularly, a statistically significant increase (or decrease) is an increase (or decrease) of a size which is considered to be statistically significant for the risk prediction. The terms "significant" and "statistically significant" are known to the person skilled in the art. Whether a increase or decrease is statistically significant can be determined without further ado by the person skilled in the art using various well known statistic evaluation tools including those referred to herein.

A preferred increase of the second ratio of sFlt-1 or Endoglin to PlGF in the second sample as compared to the first ratio of sFlt-1 or Endoglin to PlGF in the first sample which have been found in the course of the invention to be indicative for a subject who is at risk of developing at least one preeclampsia related adverse outcome after delivery of baby, preferably, is an increase of at least 3% more preferably of at least 10% and even, more preferably, of at least 20%, and most preferably of at least 30%.

A preferred decrease of the second ratio of sFlt-1 or Endoglin to PlGF in the second sample as compared to the first ratio of sFlt-1 or Endoglin to PlGF in the first sample which have been found in the course of the invention to be indicative for a subject who is not at risk of developing a preeclampsia related adverse outcome after delivery of baby, preferably, is decrease of at least 10% more preferably of at least 20% and even, more preferably, of at least 30%, and most preferably of at least 40%.

It is to be understood that the definitions and explanations of the terms made above and below apply accordingly for all embodiments described in this specification and the accompanying claims.

The present invention further relates to a method for differentiating between a subject being at risk of developing at least one preeclampsia related adverse outcome after delivery of baby and a subject being not at risk of developing a preeclampsia related adverse outcome after delivery of baby, said method comprising the steps of a) measuring in a first sample obtained from a female subject with an uneventful pregnancy before delivery of baby
  i) the level of the biomarker sFlt-1 (soluble fms-like tyrosine kinase-1) or the level of the biomarker Endoglin, and
  ii) the level of the biomarker PlGF (Placental Growth Factor),
b) calculating a first ratio of the levels of the biomarkers as measured in step a),
c) measuring in a second sample obtained from said female subject after delivery of baby the levels of the biomarkers as measured in step a),
d) calculating a second ratio of the levels measured in step c), and
e) comparing the second ratio to the first ratio.

In an embodiment, step e) of comparing the second ratio to the first ratio is carried out by calculating a ratio of the second ratio to the first ratio (or vice versa).

The present invention further relates to a method for identifying a subject being at risk of developing at least one preeclampsia related adverse outcome after delivery of baby, said method comprising the steps of a) measuring in a first sample obtained from a female subject with an uneventful pregnancy before delivery of baby
  i) the level of the biomarker sFlt-1 (soluble fms-like tyrosine kinase-1) or the level of the biomarker Endoglin, and
  ii) the level of the biomarker PlGF (Placental Growth Factor),
b) calculating a first ratio of the levels of the biomarkers as measured in step a),
c) measuring in a second sample obtained from said female subject after delivery of baby the levels of the biomarkers as measured in step a),
d) calculating a second ratio of the levels measured in step c), and
e) comparing the second ratio to the first ratio.

In an embodiment, step e) of comparing the second ratio to the first ratio is carried out by calculating a ratio of the second ratio to the first ratio (or vice versa).

In a preferred embodiment of the methods of the present invention, said methods further comprise the step of recommending and/or initiating at least one suitable supportive measure, if it is predicted that the subject is at risk of developing at least one preeclampsia related adverse outcome after delivery of baby (or if the subject is identified to be at risk of developing at least one preeclampsia related adverse outcome after delivery of baby).

As discussed before, a subject suffering from at least one preeclampsia related adverse outcome after delivery of baby requires particular medical care. Thus, if a subject is identified to be at risk of developing at least one preeclampsia related adverse outcome after delivery of baby, in particular of developing postpartum preeclampsia, postpartum eclampsia and/or postpartum HELLP syndrome such an assessment can help to establish suitable supportive measures for the subject in advance, i.e. before the preeclampsia related adverse outcome after delivery of baby becomes clinically apparent. Preferably, said at least one suitable supportive measure is selected from the group consisting of: close monitoring (in particular with respect to clinical symptoms of postpartum HELLP syndrome, postpartum preeclampsia, or postpartum eclampsia), admittance to an intensive care unit, administration of corticosteroids, admission of magnesium sulfate, and administration of blood pressure reducing agents and other specific measures dependent on the adverse outcome of the mother Haram K, Svendsen E, Abildgaard U. The HELLP syndrome: clinical issues and management. A review. BMC Pregnancy and Childbirth 2009; 9(8). dx.doi.org/10.1186/1471-2393-9-8 or DGGG. S1-Leitlinie: Diagnostik und Therapie hypertensiver Schwangerschaftserkrankungen der Deutschen Gesellschaft für Gynäkologie und Geburtshilfe, see citation above.

Accordingly, the present invention further relates to a method of initiating at least one suitable supportive measure in a female subject after delivery of baby; said method comprising the steps of the aforementioned methods of the present invention, the further step of identifying a patient as being at risk of developing at least one preeclampsia related adverse outcome after delivery of baby, and the further step of initiating at least one suitable supportive measure as outlined above.

If the subject is not at risk, the subject may be excluded from said at least one supportive measure.

The present invention further relates to the (in vitro) use of
the biomarkers sFlt-1 (or Endoglin) and PlGF, or
an agent that (specifically) binds to sFlt-1 (or an agent that (specifically) binds to Endoglin) and an agent that (specifically) binds to PlGF
in a first sample obtained from a female subject with an uneventful pregnancy before delivery of baby and in a second sample obtained from said female subject after delivery of baby for predicting the risk of a female subject to develop at least one preeclampsia related adverse outcome after delivery of baby.

The present invention further relates to the (in vitro) use of
the biomarkers sFlt-1 (or Endoglin) and PlGF, and/or
an agent that (specifically) binds to sFlt-1 (or an agent that (specifically) binds to Endoglin) and an agent that (specifically) binds to PlGF
for the manufacture of a diagnostics for predicting the risk of a female subject to develop at least one preeclampsia related adverse outcome after delivery of baby, in particular in a first sample obtained from a female subject with an uneventful pregnancy before delivery of baby and in a second sample obtained from said female subject after delivery of baby.

Preferably, the biomarkers or agents be used, as indicated in the aforementioned method.

Preferably, a first and a second ratio of sFlt-1 or Endoglin and PlGF (as described elsewhere herein) shall be calculated for the first and the second sample and the ratios shall be compared, in particular wherein an increase of the second ratio (or an essentially unchanged ratio) as compared to the first ratio is indicative for a subject who is at risk of developing at least one preeclampsia related adverse outcome after delivery of baby, and/or wherein a decrease of the second ratio as compared to the first ratio is indicative for a subject who is not at risk of developing a preeclampsia related adverse outcome after delivery of baby.

Preferably, the agent is a detection agent. In an embodiment, the agent is an antibody such as a monoclonal or polyclonal antibody.

Preferred diagnostic algorithms are disclosed herein above.

Preferably, the agent is a detection agent. In an embodiment, the agent is an antibody such as a monoclonal or polyclonal antibody.

The present invention further relates to a device adapted for predicting the risk of a female subject to develop at least one preeclampsia related adverse outcome after delivery of baby, in particular, by carrying out the aforementioned method, said device comprising:

a) an analyzer unit comprising an agent which specifically binds to sFlt-1 and/or Endoglin and an agent which specifically binds to PlGF, said unit being adapted for measuring the level of sFlt-1 and/or Endoglin and the level of PlGF in a first sample of a female subject obtained before delivery of baby and a second sample of said female subject obtained after delivery of baby; and b) an evaluation unit comprising a data processor having implemented an algorithm for carrying out the following steps of:
 i) calculating a first ratio from said levels of sFlt-1 or Endoglin and PlGF determined in the first sample and a second ratio from said levels of sFlt-1 or Endoglin and PlGF determined in the second sample; and
 ii) comparing the value of the said first and the said second ratio, and optionally
 iii) predicting the risk of said subject to develop at least one preeclampsia related adverse outcome after delivery of baby,
 in particular whereby a subject is predicted to be at risk for developing at least one preeclampsia related adverse outcome after delivery of baby if the value of the second ratio is increased (or essentially unchanged) as compared to the value of the first ratio (and/or if the ratio of the second ratio to the first ratio is equal to or larger than 1), and/or whereby a subject is predicted to be not at risk for developing a preeclampsia related adverse outcome after delivery of baby if the value of the second ratio is decreased compared to the value of the first ratio (and/or if the ratio of the second ratio to the first ratio is lower than 1).

Optionally the algorithm for carrying out the following step may further carry out the step of predicting the risk of developing at least one preeclampsia related adverse outcome after delivery of baby.

The term "device" as used herein relates to a system comprising the aforementioned units operatively linked to each other as to allow the diagnosis according to the methods of the invention. Preferred agents (i.e. detection agents) which can be used for the analyzer unit are disclosed elsewhere herein. The analyzer unit, preferably, comprises said detection agents in immobilized form on a solid support which is to be contacted to the sample comprising the biomarkers the level of which is to be determined. Moreover, the analyzer unit can also comprise a detector which measures the level of detection agent which is specifically bound to the biomarker(s). The measured level can be transmitted to the evaluation unit. Said evaluation unit comprises a data processing element, such as a computer, with an implemented algorithm for carrying out a calculation of ratios (or of biomarker levels), optionally a comparison of said calculated ratios and an evaluation of the result of the comparison by implementation of an computer based algorithm carrying out the steps of the method of the present invention set forth elsewhere herein in detail. The results may be given as output of parametric diagnostic raw data. It is to be understood that these data will usually need interpretation by the clinician. However, also envisaged are expert system devices wherein the output comprises processed diagnostic raw data the interpretation of which does not require a specialized clinician.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range).

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined level of one or more markers disclosed herein, and a suitable reference, is embodied and performed by executing the instructions. The results may be given as output of parametric diagnostic raw data or as absolute or relative levels. According to various embodiments of the system disclosed herein, a "diagnosis" may be provided by the computing device of a system disclosed herein based on said comparison of the calculated "level" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Furthermore, encompassed by the invention is a kit adapted for carrying out the aforementioned method for predicting the risk of a female subject for developing at least one preeclampsia related adverse outcome after delivery of baby comprising i) detection agents for determining the levels of the biomarkers sFlt-1 and PlGF or ii) detection agents for determining the levels of the biomarkers Endoglin and PlGF, or iii) detection agents for determining the levels of the biomarkers sFlt-1, Endoglin and/or PlGF as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a predefined level for the biomarker as referred to herein representing a reference level.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in single-use form), or multiple immobilized probes may be provided in multiple different containers. In further embodiments, the probes may be immobilized on multiple different types of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, the kits may comprise a single container or multiple containers, and where multiple containers are present, each container may be the same as all other containers, different than others, or different than some but not all other containers.

The present invention also relates to a system for predicting the risk of a female subject to develop at least one preeclampsia related adverse outcome, comprising
a) an analyzer unit configured to contact, in vitro, a portion of a first and second sample from the subject as set forth herein elsewhere with i) an agent which specifically binds PlGF, and ii) an agent which specifically binds sFlt-1, or an agent which specifically binds Endoglin,
b) an analyzer unit configured to detect a signal from the portion of the sample from the subject contacted with the agents,
c) a computing device having a processor and in operable communication with said analysis units, and
d) a non-transient machine readable media including a plurality of instruction executable by a the processor, the instructions, when executed calculate a first and a second ratio as set forth herein elsewhere, and compare the first ratio with the second ratio, thereby predicting the risk of a female subject to develop at least one preeclamsia related adverse outcome.

All references referred to above are herewith incorporated by reference with respect to their entire disclosure content as well as their specific disclosure content explicitly referred to in the above description.

EXAMPLES

The following Examples shall merely illustrate the invention. They shall not be construed, whatsoever, to limit the scope of the invention.

Example 1: Measurement of Serum Levels of PlGF, sFlt-1 and Endoglin

Serum levels of sFlt-1, PlGF and Endoglin were determined using the commercially available immunoassays. In particular, the following assays have been used.

sFlt-1 was determined with sandwich immunoassays using analyzers from the Roche Elecsys™- or cobas e™-series. The assay comprises two monoclonal antibodies specific for the respective polypeptide. The first of these antibodies is biotinylated and the second one is labelled with a Tris(2,2'-bipyridyl)ruthenium(II)-complex. In a first incubation step both antibodies are incubated with the sample. A sandwich complex comprising the peptide to be determined and the two different antibodies is formed. In a next incubation step streptavidin-coated beads are added to this complex. The beads bind to the sandwich complexes. The reaction mixture is then aspirated into a measuring cell where the beads are magnetically captured on the surface of an electrode. The application of a voltage then induces a chemiluminescent emission from the ruthenium complex which is measured by a photomultiplier. The emitted amount of light is dependent on the amount of sandwich complexes on the electrode. The sFlt-1 test is commercially available from Roche Diagnostics GmbH, Mannheim, Germany. Further details on the assay are found in the package insert. The measuring range of sFlt-1 includes levels between 10 to 85,000 pg/ml.

Endoglin was measured using the Quantikine™ Human Endoglin/CD105 immunoassay which is commercially available from R&D Systems, Inc, Minneapolis, US. This assay employs the quantitative sandwich enzyme immunoassay technique. A monoclonal antibody specific for Endoglin has been pre-coated onto a microplate. Standards and samples are pipetted into the wells and any Endoglin present is bound by the immobilized antibody. After washing away any unbound substances, an enzyme-linked monoclonal antibody specific for Endoglin is added to the wells. Following a wash to remove any unbound antibody-enzyme reagent, a substrate solution is added to the wells and color develops in proportion to the level of Endoglin bound in the initial step. The color development is stopped and the intensity of the color is measured. Further details on the assay are found in the package insert. The measuring range of Endoglin includes levels between 0.001 ng/L to 10 ng/ml.

PlGF was tested using two PlGF specific antibodies in a sandwich immunoassay which is carried out on an Elecsys™- or cobas e™-series analyzer (see above for details). The PlGF test is commercially available from Roche Diagnostics GmbH, Mannheim, Germany. Further details on the assay are found in the package insert. The measuring range of PlGF includes levels of 3 to 10,000 pg/ml.

Example 2

Analysis of the biomarkers sFlt-1 and PlGF in outcome patients which developed postpartum HELLP syndrome, postpartum preeclampsia or postpartum eclampsia and in controls. R1 represents the result of the ratio in the first sample; R2 corresponds to the result of the ratio obtained from the second sample.

Women with Postpartum HELLP Syndrome/Postpartum Preeclampsia/Postpartum Eclampsia
1) Woman with Postpartum HELLP Syndrome:
   sFlt-1/PlGF ratio (R1)=44 sFlt-1/PlGF ratio (R2)-64
   R2/R1=65/44=1.45 (>=1)
2) Woman with Postpartum Severe Preeclampsia and Asociated Hepatopathology:
   sFlt-1/PlGF ratio (R1)=162
   sFlt-1/PlGF ratio (R2)=283
   R2/R1=283/162=1.74 (>=1)
Controls
Women with Preeclampsia (Clinical Onset of Disease Before Delivery):
1) Woman with Severe Preeclampsia (Onset of Disease and Delivery in Gestational Week 33-36)
   sFlt-1/PlGF ratio (R1)=101
   sFlt-1/PlGF ratio (R2)=19
   R2/R1=19/101=0.18 (<1)

Women with No Preeclampsia/Eclampsia/HELLP Syndrome:
1) Woman with Elevated Liver Enzymes
   sFlt-1/PlGF ratio (R1)=143
   sFlt-1/PlGF ratio (R2)=73
   R2/R1=73/143=0.51 (<1)
2) Another Control Woman
   sFlt-1/PlGF ratio (R1)=132
   sFlt-1/PlGF ratio (R2)=35
   R2/R1=35/132=0.26 (<1)

In addition, the levels of sFlt-1 and PlGF in the sample obtained after delivery were compared to the levels of sFlt-1 and PlGF in the sample obtained before delivery. Interestingly, both levels decreased after delivery in subjects with postpartum preeclampsia related adverse outcomes. Based on the observed decrease, it was not possible to establish a risk prediction for the tested patients based on the levels of the single biomarker sFlt-1 or PlGF alone respectively (as compared to the controls). Thus, the ratio as disclosed herein is a reliable marker for predicting the risk of postpartum preeclampsia related adverse outcomes.

The invention claimed is:

1. A method for predicting the risk of a female subject to develop at least one preeclampsia related adverse outcome after delivery of baby, said method comprising the steps of
   a) measuring in a first sample obtained from a female subject before delivery of baby
      i) the level of the biomarker sFlt-1 (soluble fms-like tyrosine kinase-1) or the level of the biomarker Endoglin, and
      ii) the level of the biomarker PlGF (Placental Growth Factor),
   b) calculating a first ratio of the levels of the biomarkers as measured in step a),
   c) measuring in a second sample obtained from said female subject after delivery of baby the levels of the biomarkers as measured in step a),
   d) calculating a second ratio of the levels measured in step c),
   e) comparing the second ratio to the first ratio,
   f) identifying a subject who is at risk to develop at least one preeclampsia related adverse outcome based on the comparison of step e), wherein the first and the second ratio are the ratios of sFlt-1 to PlGF, or of Endoglin to PlGF, and wherein an increase of the second ratio, or a change of less than 7% of the second ratio as compared to the first ratio is indicative of a subject who is at risk of developing at least one preeclampsia related adverse outcome after delivery of baby, or wherein a decrease of 7% or greater of the second ratio as compared to the first ratio is indicative of a subject who is not at risk of developing a preeclampsia related adverse outcome after delivery of baby; and
   g) administering a treatment to the subject identified as at risk, wherein the treatment is selected from the group consisting of a corticosteroid, administration of magnesium sulfate, and/or administration of a blood pressure reducing agent;
   wherein said measuring steps are carried out by contacting the sample with antibodies or antibody fragments specific for the particular biomarker measured, and wherein the first sample is obtained within 48 hours before the delivery of the baby and the second sample is obtained within 24 hours after delivery of the baby.

2. The method of claim 1, wherein in steps a) and c) the levels of the biomarkers sFlt-1 and PlGF are measured.

3. The method of claim 2, wherein the at least one preeclampsia related adverse outcome is selected from the group consisting of postpartum preeclampsia, postpartum eclampsia and postpartum HELLP syndrome.

4. The method of claim 1, wherein the subject is human.

5. The method of claim 1, wherein the sample is a blood, serum or plasma sample, or wherein the sample is a urine sample.

6. The method of claim 1, wherein the risk of developing at least one preeclampsia related adverse outcome is predicted within seven days after delivery of baby.

7. The method of claim 1, wherein the female subject has not experienced pre-eclampsia, eclampsia and/or HELLP syndrome before delivery of baby.

8. The method of claim 1, wherein the female subject has not experienced pre-eclampsia, eclampsia and/or HELLP syndrome.

9. A method for predicting the risk of a female subject to develop at least one preeclampsia related adverse outcome after delivery of baby, said method comprising the steps of
   a) measuring in a first sample obtained from a female subject before delivery of baby
      i) the level of the biomarker sFlt-1 (soluble fms-like tyrosine kinase-1) or the level of the biomarker Endoglin, and
      ii) the level of the biomarker PlGF (Placental Growth Factor),
   b) calculating a first ratio of the levels of the biomarkers as measured in step a),
   c) measuring in a second sample obtained from said female subject after delivery of baby the levels of the biomarkers as measured in step a),
   d) calculating a second ratio of the levels measured in step c),
   e) comparing the second ratio to the first ratio,
   f) identifying a subject who is at risk to develop at least one preeclampsia related adverse outcome based on the comparison of step e), wherein the first and the second ratio are the ratios of PlGF to sFlt-1, or of PlGF to Endoglin, and wherein decrease of the second ratio or a change of less than 7% of the second ratio as compared to the first ratio is indicative of a subject who is at risk of developing at least one preeclampsia related adverse outcome after delivery of baby, and/or wherein an increase of 7% or greater of the second ratio as compared to the first ratio is indicative of a subject who is not at risk of developing a preeclampsia related adverse outcome after delivery of baby; and
   g) administering a treatment to the subject identified as at risk, wherein the treatment is selected from the group consisting of a corticosteroid, administration of magnesium sulfate, and/or administration of a blood pressure reducing agent;
wherein said measuring steps are carried out by contacting the sample with antibodies or antibody fragments specific for the particular biomarker measured, and wherein the first sample is obtained within 48 hours before the delivery of the baby and the second sample is obtained within 24 hours after the delivery of the baby.

* * * * *